United States Patent [19]

Tanaka et al.

[11] Patent Number: 5,728,792

[45] Date of Patent: Mar. 17, 1998

[54] METHOD FOR PREPARING WATER ABSORBENT RESIN

[75] Inventors: Keiji Tanaka, Kyoto-fu; Masashi Date, Osaka-fu; Kenjiro Tsubota; Tsuyoshi Yuki, both of Kyoto-fu; Satoshi Tamabuchi, Osaka-fu, all of Japan

[73] Assignee: Sanyo Chemical Industries, Ltd., Kyoto-Fu, Japan

[21] Appl. No.: 675,405

[22] Filed: Jul. 2, 1996

[30] Foreign Application Priority Data

Jul. 18, 1995 [JP] Japan ................................. 7-205370

[51] Int. Cl.$^6$ ..................... C08F 220/06; C08F 222/38; C08F 283/02; C08G 83/00
[52] U.S. Cl. ................... 526/307.6; 526/63; 525/426; 527/314
[58] Field of Search ...................... 526/307.6, 63; 525/329.7

[56] References Cited

U.S. PATENT DOCUMENTS

| | | |
|---|---|---|
| 4,857,610 | 8/1989 | Chmelir et al. ........................ 526/88 |
| 5,385,983 | 1/1995 | Graham ............................... 525/330.1 |
| 5,506,324 | 4/1996 | Gartner et al. ...................... 526/318.41 |

FOREIGN PATENT DOCUMENTS

| | | |
|---|---|---|
| 60-55002 | 3/1985 | Japan. |
| 2-14361 | 4/1990 | Japan. |
| 4-175319 | 6/1992 | Japan. |

*Primary Examiner*—Joseph L. Schofer
*Assistant Examiner*—Wu C. Cheng
*Attorney, Agent, or Firm*—Merchant, Gould, Smith, Edell, Welter & Schmidt, P.A.

[57] ABSTRACT

A method for producing a water absorbent resin by polymerizing a water-soluble monomer having a polymerizable unsaturated group (A) and a crosslinking agent (B) as the essential components by radical polymerization in the presence of water or, polymerizing a water-soluble monomer having an unsaturated group (A) and a crosslinking agent (B) by radical-graft copolymerization with a water-soluble polymer (C) as the backbone polymer in the presence of water, wherein a water-based solid material capable of being endothermally fused or dissolved into water (D) is added when initiating the polymerization, with at least a part of the water-based solid material (D) in a solid state. By the method of the present invention, a water absorbent resin having a high molecular weight and a high absorption capacity with little water-soluble component can be obtained with ease.

6 Claims, No Drawings

METHOD FOR PREPARING WATER ABSORBENT RESIN

BACKGROUND OF THE INVENTION

1. Field of the Invention

This invention relates to a method for producing water absorbent resins, and more specifically, to a polymerization method for producing water absorbent resins having excellent absorption ability.

2. Description of the Prior Art

In general, the absorption ability of a water absorbent resin comprising a polymer of a water soluble monomer having a polymerizable unsaturated group as the main chain increases as the molecular weight of the main chain becomes larger. In order to provide a water absorbent resin having a high molecular weight by polymerizing a water soluble monomer and a crosslinking agent with a small amount of a polymerization initiator to an appropriate concentration, a rise in the temperature of the polymerizable monomer solution resulting from the polymerization heat should be avoided.

To realize a high molecular weight by avoiding the rise in temperature, methods of polymerizing while eliminating heat using a special polymerizing device to facilitate cooling off of the hydrogel obtained by the polymerization have been proposed, such as a method of polymerizing in a sheet form or a method of facilitating the cooling efficiency by the use of a device to stir for increasing the surface area to be cooled while pulverizing the proposed in JP-B-2-14361 and JP-A-4-175319.

However, in the above mentioned conventional production methods, heat elimination is not efficient enough to provide a water absorbent resin having a sufficiently high molecular weight. Thus, there have been problems including difficulty in producing a water absorbent resin having a good absorption ability and the need of a complicated production device.

SUMMARY OF THE INVENTION

It is an object of the present invention to provide a method for producing a water absorbent resin having an excellent absorption ability.

It is another object of the present invention to provide a method for producing a water absorbent resin having a polymer main chain with a large molecular weight, an excellent absorption ability and little water soluble component.

It is a further object of the present invention to provide a method for producing a water absorbent resin having an excellent water absorption ability without the need of a complicated production device.

In order to achieve the above mentioned objects, the inventors of the present invention discovered a method of introducing a solid material capable of being endothermally fused or dissolved into water, such as ice, into the reaction container to achieve the present invention.

The present invention relates to a method for producing a water absorbent resin by polymerizing a water-soluble monomer having a polymerizable unsaturated group (A) and a crosslinking agent (B) by radical polymerization or, polymerizing a water soluble monomer having an unsaturated group (A) and a crosslinking agent (B) by radical-graft copolymerization with a water soluble polymer (C) as the backbone polymer in the presence of water, wherein a water-based solid material capable of being endothermally fused or dissolved into water (D) is added when initiating the polymerization, with at least a part of the water-based solid material (D) in a solid state.

DESCRIPTION OF THE PREFERRED EMBODIMENT

Examples of a water-soluble monomer having an unsaturated group (A) of this invention include monomers having a polymerizable unsaturated group containing an acid group such as a carboxylic acid group, a sulfonic acid group and a phosphoric acid group, and salts thereof.

Examples of water-soluble monomers having a polymerizable unsaturated group and containing a carboxylic acid group include unsaturated mono- or poly- carboxylic acids of from 3 to 9 carbon atoms such as (meth)acrylic acid (which denotes acrylic acid and/or methacrylic acid, and this applies to the disclosure hereinafter), crotonic acid, sorbic acid, maleic acid, itaconic acid, cinnamic acid; and anhydrides thereof such as maleic anhydride.

Examples of water-soluble monomers having a polymerizable unsaturated group and containing a sulfonic acid group include aliphatic vinyl sulfonic acids of 2 to 8 carbon atoms or aromatic vinyl sulfonic acids of 8 to 14 carbon atoms such as vinyl sulfonic acid, allyl sulfonic acid, vinyl toluene sulfonic acid and styrene sulfonic acid; (meth) acrylic alkyl sulfonic acids such as sulfoethyl (meth)acrylate and sulfopropyl (meth)acrylate; and (meth) acrylamide alkyl sulfonic acids such as 2-acrylamide-2-methyl propane sulfonic acid.

Examples of water-soluble monomers having a polymerizable unsaturated group and containing a phosphoric acid group include phosphoric acid monoesters of hydroxy alkyl (meth)acrylate having a hydroxy alkyl group of 2 to 4 carbon atoms such as 2-hydroxyethyl (meth)acryloyl phosphate and phenyl-2-acryloyloxyethyl phosphate.

Examples of salts of monomers having a polymerizable unsaturated group and containing an acid group include alkali metal salts such as salts of sodium, potassium or lithium; alkali earth metal salts such as salts of calcium or magnesium; and ammonium salts or amine salts such as alkylamine salts having 1 to 6 carbon atoms including methyl amine salt or trimethyl amine salt, and alkanol amine salts such as triethanol amine salt and diethanol amine salt.

Such water-soluble monomers can be used alone or in combinations of two or more. Among the above-mentioned examples, water soluble monomers having a polymerizable unsaturated group containing a carboxylic acid group or sulfonic acid group and sodium salts or potassium salts thereof are preferable, particularly preferable are water soluble monomers having a polymerizable unsaturated group containing a carboxylic acid group and sodium salts thereof.

The neutralization degree of the water-absorbent resins obtained in a method of the present invention is preferably 50 to 90 mole %, more preferably 60 to 80 mole %. When the neutralization degree is from 50 to 90 mole %, since the viscosity of the obtained hydrogel polymer after polymerization does not increase too much, the water absorbent resin can be produced with good operability, and thus it is preferable. Further, since the pH of the obtained polymer does not become too high, thus not providing irritation to human skin, it is preferable in terms of safety.

The neutralization can be carried out at an optional stage of water-absorbent resin production, such as in the stage of water-soluble monomers having a polymerizable unsaturated group (A) and in the stage of a hydrogel as a polymerization product.

In the present invention, a water-insoluble monomer can be used optionally with the above mentioned water-soluble monomers (A). In this case, a conventional water insoluble monomer can be used. Examples of the water-insoluble monomers include methyl acrylate, acrylonitrile, styrene and vinyl acetate.

The ratio of the above mentioned water-insoluble monomer based on the water-soluble monomer (A) is in general, 20 mole % or less, preferably 10 mole % or less. If the ratio exceeds 20 mole %, the water absorbency of the obtained polymer may be adversely affected.

Examples of crosslinking agents (B) include compounds having two polymerized double bonds (B1) and compounds having at least one polymerized double bond and at least one functional group reactive with the water-soluble monomer (B2).

Examples of the above-mentioned crosslinking agents (B1) include the following:

① bis(meth)acrylamide

N,N'-alkylene bis(meth)acryl amide having an alkylene group of 1 to 6 carbon atoms, such as N,N'-methylene bisacrylamide.

② di- or poly- ester of polyols and unsaturated mono- or poly-carboxylic acid di- or tri- (meth)acrylate of polyols (such as ethylene glycol, trimethylol propane, glycerol, polyoxyethylene glycol and polyoxypropylene glycol);

unsaturated polyester obtained by the reaction of the above-mentioned polyols and an unsaturated acid (such as maleic acid); and di- or tri- (meth)acrylic ester obtained by the reaction of polyepoxide and (meth) acrylic acid.

③ carbamyl ester carbamyl ester obtained by the reaction of hydroxyethyl (meth)acrylate and a polyisocyanate (such as tolylene diisocyanate, hexamethylene diisocyanate, 4, 4'-diphenyl methane diisocyanate, or NCO group-containing prepolymers obtained by the reaction of the above-mentioned polyisocyanates and a compound having active hydrogen atoms).

④ di- or poly- vinyl compound divinyl benzene, divinyl toluene, divinyl xylene, divinyl ether, divinyl ketone, trivinyl benzene, etc.

⑤ di- or poly- (meth)allyl ether of polyols di- or poly- (meth)allyl ether of polyols such as alkylene glycol, glycerol, polyalkylene glycol, polyalkylene polyol and carbohydrate. For example, polyethylene glycol diallyl ether, allylated starch, and allylated cellulose are included.

⑥ di- or poly- allylester of polycarboxylic acid diallyl phthalate, diallyl adipate, etc.

⑦ ester of unsaturated mono- or poly- carboxylic acid and mono(meth)allyl ether of polyol (meth)acrylate of polyethylene glycol monoallyl ether.

⑧ allyloxy alkane tetra allyloxy ethane, pentaerythritol triallyl ether, etc.

Examples of the crosslinking agents (B2) include ethylenically unsaturated compounds having a group reactive with (meth)acrylic acid and/or other copolymerizable monomers including a group reactive with a group such as a carboxyl group or carboxylic anhydride group, for example, a hydroxyl group, an epoxy group and a cationic group. Specific examples are unsaturated compounds having a nonionic group, including unsaturated compounds having a hydroxy group such as N-methylol (meth)acrylamide; unsaturated compounds having an epoxy group such as glycidyl (meth)acrylate; unsaturated compounds having a cationic group including unsaturated compounds having a quarternary ammonium salt group such as N,N,N-trimethyl-N-(meth)acryloyloxyethyl trimethyl ammonium chloride, N,N, N-trimethyl-N-(meth)acryloyloxyethyl ammonium chloride; and unsaturated compounds having a tertiary amino group such as dimethyl amino ethyl (meth)acrylate and diethyl amino ethyl (meth)acrylate.

The above-mentioned crosslinking agents (B1), (B2) can be used in combinations of two or more.

In crosslinking agents (B), crosslinking agents (B1) are preferable. In particular, bis(meth)acrylamide, di- or polyester of polyols with unsaturated monocarboxylic acids and allyloxy alkanes are preferable. Further, N,N'-methylene bisacrylamide, ethylene glycol diacrylate, trimethylolpropane triacrylate and tetra allyloxy ethane are more preferable.

The ratio of the crosslinking agent (B) to the total weight of the water-soluble monomer (A) and crosslinking agent (B) is generally 0.0001 to 10 weight %, preferably 0.001 to 5 weight %, more preferably 0.01 to 2 weight %. If the ratio is less than 0.0001 weight %, the gel strength of the obtained resin at the time of water absorption becomes so small that the resin becomes a sol. On the other hand, if the ratio exceeds 10 weight %, the gel strength becomes so large that the absorption ability becomes deteriorated.

In a method of the present invention, a water-absorbing polymer is produced by polymerizing a water-soluble monomer having a polymerizable unsaturated group (A) and a crosslinking agent (B) by radical polymerization or, polymerizing a water-soluble monomer having an unsaturated group (A) and a crosslinking agent (B) by radical graft-copolymerization with a water-soluble polymer (C) as the backbone polymer. Examples of water-soluble polymers (C) include polysaccharides (C1) and synthetic water soluble polymers (C2).

Examples of such polysaccharides (C1) include starches, celluloses and their derivatives. Examples of starches include raw starches such as sweet potato starch, potato starch, wheat starch, corn starch and rice starch; processed starches such as oxidized starch, dialdehyde starch, alkyl etherified starch, allyletherified starch, oxyalkylated starch and aminoethyl etherified starch.

Examples of celluloses include celluloses obtained from lumber, leaves, stalks, basts and seed fibers; and processed celluloses such as alkyl etherified cellulose, organic acid esterified cellulose, oxidized cellulose and hydroxyalkyl etherified cellulose.

Examples of water-soluble polymers (C2) include water-soluble polyesters such as polyethylene terephthalate obtained by copolymerizing sodium sulfoisophthalate, and water-soluble polyethers such as polyethylene glycol.

When a water-soluble polymer (C) is used as the backbone polymer, the ratio of (C) to a water-soluble monomer having a polymerizable unsaturated group (A) is in general, 30 weight % or less, preferably from 3 to 20 weight %. If the ratio of (C) exceeds 30 weight %, the water-absorbing ability of the obtained water-absorbent resin is likely to deteriorate.

Examples of water-based solid materials capable of being endothermally fused or dissolving into water (D) are selected from the group consisting of ice, which is endothermally fused; ice which contains a salt having a property of being endothermally dissolving in water (such as ammonium chloride and ammonium nitrate); ice which contains an unpolymerizable organic compound having a property of being endothermally dissolving in water (such as urea); and ice which contains a water-soluble monomer (A).

The total dissolved amount of these salts, unpolymerizable organic compounds and monomers (A) are preferably contained in (D) within the range that the solidifying point of (D) becomes 0° C. or lower. Further, in order to facilitate uniform dispersion of (D) into the liquid before polymerization, it is preferable that the absolute value of the difference between the specific gravity of (D) and the specific gravity of the liquid phase at the polymerization is 0.3 g/ml or smaller.

It is preferable to use a water-based solid material (D) obtained by freezing a liquid with a dissolved oxygen concentration of 1 ppm or less, preferably 0.5 ppm or less. In this case, water, water containing a salt having a property of endothermally dissolved in water and/or water containing a water soluble monomer (A) can be used as the "liquid".

The ratio of a water-based solid material (D) based on the total weight of a water-soluble monomer (A) (including any monomer (A) dissolved in (D)), (B), (C), (D) and water is in general, 5 to 50 weight %, and preferably 10 to 35 weight % in terms of the balance of the endothermic effect and the quality of the obtained polymer.

As the method of polymerizing in the presence of water in the present invention, a conventional method can be used as long as a water-based solid material (D) capable of being endothermally fused in a polymerizable monomer solution or endothermally dissolved in water is mixed. Examples of such polymerization methods include aqueous solution polymerization, suspension polymerization, and reverse phase suspension polymerization using a radical polymerization catalyst. Further, as a method of initiating polymerization, a method of irradiating with radioactive ray, electron beam or ultraviolet ray can be adopted. A preferable polymerization method is the aqueous solution polymerization.

Examples of radical polymerization catalysts include azo compounds such as azobisisobutyronitrile, azobiscyanovaleric acid and 2,2'-azobis(2-amidinopropane)hydrochloride; inorganic peroxides such as hydrogen peroxide, ammonium persulfate, potassium persulfate and sodium persulfate; organic peroxides such as benzoyl peroxide, di-t-butyl peroxide, cumene hydro peroxide, succinic peroxide and di(2-ethoxy ethyl)peroxydicarbonate; and redox catalysts comprising the combination of reducing agent (such as a sulfite salt or a bisulfite salt of an alkali metal, ammonium sulfite, ammonium bisulfite, ascorbic acid) and an oxidizing agent (such as persulfate of an alkali metal, ammonium persulfate, peroxides); and the combination of two or more of these.

Redox catalysts comprising the combination of hydrogen peroxide and ascorbic acid, hydrogen peroxide and ferrous sulfate, or sodium persulfate and sodium bisulfite can be used as well.

Among these examples, redox catalysts, and a combination of a redox catalyst and an azo compound are preferable.

The amount of the catalysts is similar to those used in conventional methods, generally 0.0001 to 5 weight %, preferably 0.0005 to 1 weight % based on the total weight of the monomers and the crosslinking agent.

As to polymerization initiating temperature, polymerization can be started from a low temperature owing to the presence of (D). As to other polymerization conditions such as polymerization concentration and aging temperature, conventional conditions can be applied. For example, polymerization initiating temperature of −10° C. to 10° C., polymerization concentration of 10 to 40 weight %, and aging time of 5 hours to 12 hours can be applied.

The hydrogel after polymerization preferably can be dried and pulverized into a powder-like form by a conventional method. Examples of drying methods include a method of loading the material on porous plates, wire gauzes, flat plates, or belts and drying by batch or drying continuously, a method of hot-air drying in a rotary kiln or a fluidized drying oven, a method of heat drying by contact with the surface of a hot plate or a hot roller, and a method of heat drying with a reduced pressure.

Examples of pulverizing methods include a method of pulverizing with a pin mill or a roll mill.

The surface of the powdery water absorbent resin obtained in the present invention may be further processed by conventional surface crosslinking using a cross linking agent such as polyglycidyl ether compounds including ethylene glycol diglycidyl ether, polyamine compounds including ethylene diamine, polyol compounds including ethylene glycol and polyvalent metal compounds including sodium alminum sulfate.

Since a water absorbent resin of the present invention obtained in a method as heretofore mentioned has a high molecular weight in the main chain portion, a high absorption property can be achieved with little water soluble component.

The water absorbent resin obtained in the present invention has an absorption property of 60 to 80 g/g in general, preferably 62 to 75 g/g at an ordinary pressure. The water absorbent resin obtained in the present invention has a ratio of the water soluble component of 1 to 10 weight % in general, preferably 2 to 8 weight %.

Although the present invention will be further explained with reference to Examples and Comparative Examples, the present invention is not limited only to the embodiments described herein.

The absorption amount and the water soluble component amount of a water absorbent resin described in Examples and Comparative Examples are the values calculated by the following operation.

<Absorption capacity>

1.00 g of the water absorbent resin exactly measured was placed in a 250 mesh nylon tea bag and immersed in a 0.9 weight % aqueous solution of sodium chloride for one hour. After draining the excess solution for 15 minutes, the weight (a) g was measured. Also, the same procedure was conducted with the bag not having the sample therein and the weight (b) g was measured. The absorption capacity was calculated from the following formula.

$$\text{Absorption capacity } (g/g) = ((a)-(b))-1$$

<Water soluble component amount>

1.0 g of the water-absorbent resin exactly measured and 249 g of an aqueous solution of sodium chloride having 0.9 weight % concentration were placed in a 300-ml beaker and stirred for three hours for extraction of water-soluble component. After filtration with a filter paper, 20 ml of the sample was diluted with 30 ml of deionized water and then examined by potentiometric titration using an aqueous solution of KOH of $\frac{1}{50}$N and an aqueous solution of HCl of $\frac{1}{20}$N. The detected amount of polyacrylic acid and a salt thereof was defined as the water soluble component amount.

<Intrinsic viscosity [η]>

Since the molecular weight of a water-insoluble crosslinking polymer can not be measured, the intrinsic viscosity [η] of the polymer polymerized without a crosslinking agent was measured and the result was included in Table 1 as a datum for comparing the molecular weights in the main chain of the water absorbent resins. The intrinsic viscosity

[η] is a viscosity of the solution obtained by dissolving a gel obtained by polymerizing a monomer without a crosslinking agent in an aqueous solution of NaOH of 2N measured at 30° C.

EXAMPLE 1

196 g of acrylic acid, 0.05 g of methylenebisacrylamide as a crosslinking agent, 525 g of deionized water and 150 g of crushed ice having an average diameter of approximately 5 mm, made from deionized water having a dissolved oxygen amount of 0.05 ppm, were mixed and the polymerizable monomer solution was prepared. The mixture liquid was placed in a polymerizing vessel that allows adiabatic polymerization. By introducing nitrogen gas thereto, the dissolved oxygen amount in the solution was reduced to 0.1 ppm or less and the liquid temperature dropped to −6° C. At this time, a part of the ice remained undissolved. Then 0.03 g of an aqueous solution of hydrogen peroxide having 35 weight % concentration, 0.005 g of ascorbic acid, and 0.05 g of a radical polymerization azo catalyst "V-50" commercially available from Wako Pure Chemical Industries, Ltd. were added thereto. After 10 minutes, a temperature rise to show the initiation of polymerization was observed. After approximately 3 hours, the temperature of the solution reached equilibrium at 56° C. After a 4 hour maturation period, a polymerized hydrogel was obtained.

After pulverizing 600 g of the polymerized hydrogel with a gel chopper, 165 g of an aqueous solution of NaOH having 48 weight % concentration was added thereto. Then the solution was further mixed uniformly by means of the gel chopper. The obtained neutralized gel was dried with hot-air at 130° C. followed by pulverization by means of a mixer for domestic use to have a particle size of 20 mesh or smaller, and a water-absorbing resin of the present invention was obtained.

The polymerization initiating temperature and the polymerization maximum temperature; the absorption capacity, water-soluble component amount of the water-absorbent resin; and the intrinsic viscosity [η] of a water-soluble resin polymerized in the same conditions but without a crosslinking agent are described in Table 1.

EXAMPLE 2

A water absorbent resin of the present invention was obtained in the same conditions as Example 1 except that 196 g of acrylic acid, 525 g of deionized water and 150 g of crushed ice were replaced by 98 g of acrylic acid, 337 g of deionized water, and 436 g of a solidified material comprising 338 g of water and 98 g of acrylic acid obtained by solidifying deionized water having a dissolved oxygen concentration of 0.05 ppm and acrylic acid at a temperature of −15° C.

The polymerization initiating temperature and the polymerization maximum temperature; the absorption capacity, water soluble component amount of the water-absorbent resin; and the intrinsic viscosity [η] of a water-soluble resin polymerized in the same conditions but without a crosslinking agent are described in Table 1.

EXAMPLE 3

196 g of acrylic acid, 165 g of an aqueous solution of NaOH having 48 weight % concentration, 0.05 g of methylenebisacrylamide, and 280 g of deionized water were mixed. And the polymerizable monomer solution was adjusted to have the liquid temperature of 15° C. The mixture liquid was placed in a polymerizing vessel which allows adiabatic polymerization. By introducing nitrogen gas thereto, the dissolved oxygen concentration in the solution was reduced to 0.1 ppm or less. Then 0.03 g of an aqueous solution of hydrogen peroxide having 35 weight % concentration, 0.005 g of ascorbic acid, 0.05 g of a radical polymerization azo catalyst "V-50" commercially available from Wako Pure Chemical Industries, Ltd. were added thereto. Then, 150 g of crushed ice having an average diameter of approximately 5 mm made from deionized water having a dissolved oxygen amount of 0.05 ppm was added and stirred immediately. The liquid temperature dropped to −4° C. and the polymerizable monomer solution became sherbet-like. At this time, a part of the ice remained undissolved. After 10 minutes, a temperature rise to show the initiation of polymerization was observed. After approximately 3 hours, the temperature of the solution reached equilibrium at 52° C. After a 4 hour maturation period, the polymerized hydrogel was obtained.

791 g of the polymerized hydrogel was crushed with a gel chopper, and was dried with hot-air at 130° C. followed by pulverization by means of a mixer for domestic use to a particle size of 20 mesh or smaller, and a water-absorbing resin of the present invention was obtained.

The polymerization initiating temperature and the polymerization maximum temperature; the absorption capacity, water-soluble component amount of the water-absorbent resin; and the intrinsic viscosity [η] of a water-soluble resin polymerized in the same conditions but without a crosslinking agent are described in Table 1.

Comparative Example 1

A water-absorbent resin was obtained in the same conditions as Example 1 except that 525 g of deionized water and 150 g of crushed ice were replaced by 675 g of deionized water.

The polymerization initiating temperature and the polymerization maximum temperature; the absorption capacity, water-soluble component amount of the water-absorbent resin; and the intrinsic viscosity [η] of a water-soluble resin polymerized in the same conditions but without a crosslinking agent are described in Table 1.

Comparative Example 2

A water-absorbent resin was obtained in the same conditions as Example 3 except that 280 g of deionized water and 150 g of crushed ice were replaced by 430 g of deionized water.

The polymerization initiating temperature and the polymerization maximum temperature; the absorption capacity, water-soluble component amount of the water-absorbent resin; and the intrinsic viscosity [η] of a water-soluble resin polymerized in the same conditions but without a crosslinking agent are described in Table 1.

TABLE 1

| | polymerization state | | absorption | water-soluble | |
| --- | --- | --- | --- | --- | --- |
| | initiating temperature | maximum temperature | capacity (g/g) | component amount (%) | [η] |
| Example 1 | −5° C. | 56° C. | 68 | 3 | 9 |
| Example 2 | −8° C. | 51° C. | 69 | 3 | 10 |
| Example 3 | −4° C. | 61° C. | 62 | 4 | 8 |

TABLE 1-continued

| | polymerization state | | absorption | water-soluble | |
|---|---|---|---|---|---|
| | initiating temperature | maximum temperature | capacity (g/g) | component amount (%) | [η] |
| Comparative Example 1 | 5° C. | 69° C. | 59 | 9 | 6 |
| Comparative Example 2 | 15° C. | 84° C. | 52 | 10 | 5 |

As is apparent from Table 1, water absorbent resins obtained by the method of the present invention have a larger molecular weight of the main chain because an intrinsic viscosity [η] of the uncrosslinked water-soluble polymer polymerized in the same conditions was a high value. Further, water absorbent resins of the present invention have a higher absorption capacity and very little water soluble component. As heretofore mentioned, by adding ice having a temperature of approximately 0° C. in the polymerization stage, the molecular weight can be increased with an efficient heat removing effect and convenience.

Since water-absorbent resins of the present invention have the above-mentioned advantages, they are useful in various industrial applications such as; an application for contact with a human body such as water-absorbing pads and hygienic materials including disposable diapers for infants or adults, sanitary napkins, hygienic cottons, bandages, incontinence pads and paper towels; an application with possibility of contacting to foods such as freshness retaining materials for vegetables and fruits or drip absorbers for meat or marine products; an application for water retaining materials for plants or soils; and an application for anti-dewing agents for interior materials.

What is claimed is:

1. A method for producing a water absorbent resin by polymerizing a water-soluble monomer (A) having a polymerizable unsaturated group and a crosslinking agent (B) by radical polymerization in the presence of water or, polymerizing a water-soluble monomer (A) having an unsaturated group and a crosslinking agent (B) by radical-graft copolymerization with a water-soluble polymer (C) as the backbone polymer in the presence of water, wherein a water-based solid material (D) capable of being endothermally fused or dissolved into water is added to a monomer-containing aqueous phase when initiating the polymerization, with at least a part of the solid material (D) in a solid state.

2. The method for producing a water-absorbent resin according to claim 1, wherein the water-based solid material (D) is selected from the group consisting of ice, ice which contains a salt having a property of being endothermally dissolved in water, ice which contains an unpolymerizable organic compound having a property of being endothermally dissolved in water, and ice which contains the water soluble monomer (A).

3. The method for producing a water-absorbent resin according to claim 2, wherein the water-based solid material (D) is prepared by freezing a liquid having a dissolved oxygen concentration of 1 ppm or less.

4. The method for producing a water-absorbent resin according to claim 1, wherein the polymerization in the presence of water is an aqueous solution polymerization, using a redox catalyst, or a redox catalyst and a water-soluble azo catalyst as the polymerization catalyst.

5. The method of claim 1, wherein polymerization is initiated at a temperature in the range of −10° to 10° C.

6. The method of claim 5, wherein the temperature is in the range of −8° to −4° C.

* * * * *